United States Patent
Spolaczyk et al.

(10) Patent No.: US 6,803,594 B2
(45) Date of Patent: Oct. 12, 2004

(54) MEASURING SYSTEM FOR OPTICALLY DETERMINING CONCENTRATION OF TURBID LIQUID SAMPLES

(75) Inventors: Reiner Spolaczyk, Hamburg (DE); Kurt Harnack, Tangstedt (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 10/204,739
(22) PCT Filed: Feb. 6, 2001
(86) PCT No.: PCT/EP01/01255
§ 371 (c)(1), (2), (4) Date: Aug. 22, 2002
(87) PCT Pub. No.: WO01/63253
PCT Pub. Date: Aug. 30, 2001

(65) Prior Publication Data
US 2003/0010941 A1 Jan. 16, 2003

(30) Foreign Application Priority Data
Feb. 24, 2000 (DE) ........................ 100 08 517

(51) Int. Cl.[7] .............................................. G01N 15/06
(52) U.S. Cl. ...................................... 250/574; 250/575

(58) Field of Search ................................. 250/573–577, 250/564, 565; 356/335–343

(56) References Cited

U.S. PATENT DOCUMENTS 3,553,462 A * 1/1971 Johnson ..................... 250/565
5,140,168 A * 8/1992 King ......................... 250/575

FOREIGN PATENT DOCUMENTS

DE 195 35 046 * 3/1997

* cited by examiner

Primary Examiner—Thanh X. Luu
(74) Attorney, Agent, or Firm—Sidley Austin Brown & Wood, LLP

(57) ABSTRACT

Optical measuring system for determining the concentration, particularly of turbid liquid samples, comprising a measuring volume for taking up the liquid samples to be measured, a plurality of several photometric channels, each comprising a light source and a light sensor on opposite sides of the sample volume aligned on a common optical axis, the optical axes thereof being disposed under different azimutal angles respective to the sample volume, and an analyzing device which evaluates the concentration of the liquid samples to be measured according to the data provided by the light sensors belonging to a plurality of different photometric channels.

Figure 1:
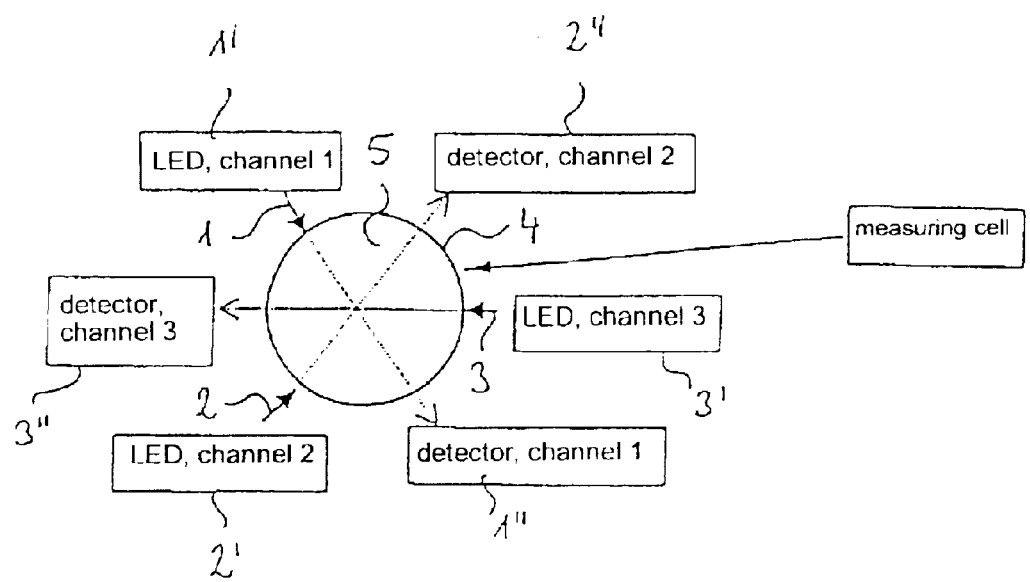

26 Claims, 9 Drawing Sheets dependence of the signals from the twist angle of the pipette point, averaged about the 3 channels, with a latex suspension.

average value of the extinction of the 3 measuring channels and extrapolation of the linear dependence for small concentrations.

average value of the scattered light portion of the 6 measuring combinations and extrapolation of the linear dependence for small concentrations.

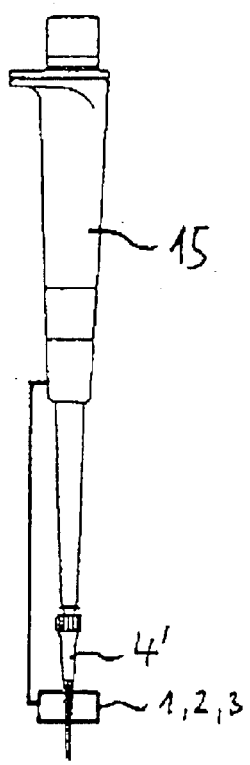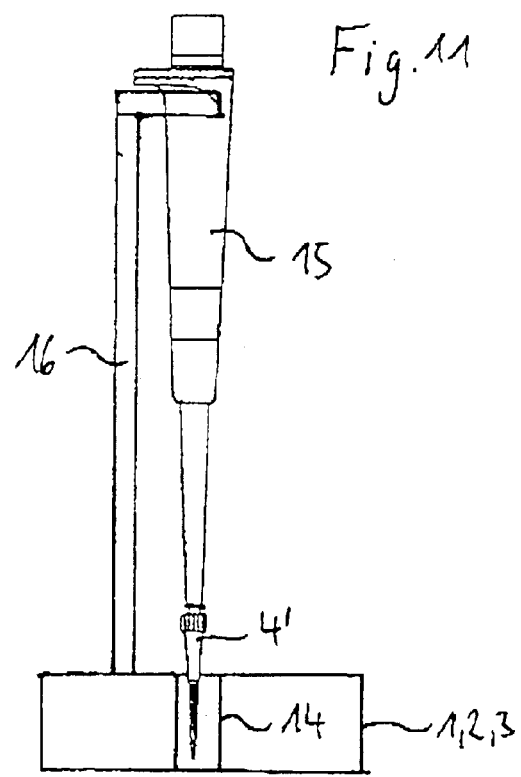

MEASURING SYSTEM FOR OPTICALLY DETERMINING CONCENTRATION OF TURBID LIQUID SAMPLES

The present invention relates to an optical measuring system to determine the concentration of liquid samples, especially the concentration of turbid liquid samples In absorption spectrometry (absorption photometry) the attenuation of light upon passing through a liquid sample is measured and displayed as extinction. The attenuation of the incident light occurs by absorption, the direction of light at this point remaining unaltered.

Turbidity measurement serves to determine the scattering centers in turbid liquid samples. For this purpose one can measure the intensity of scattered light that emerges in a defined angle from the sample hit by an incident light beam. The scattering of the light can be determined either by measuring the intensity decrease of the incident light beam after passing through the turbid medium, or by measuring the intensity of the laterally deflected light. In the first case, one speaks of the method of turbidimetry, and in the second of that of nephelometry. An important application is the measurement of the concentration of liquid cell- or bacteria cultures.

With the known optical measuring systems for absorption spectroscopy and with those for turbidity measurement, it is disadvantageous that they comprise special measuring cells for the accommodation of liquid samples, which have to be arranged in an optical path between a light emitter and a light sensor for measuring, and must be produced very accurately to maintain the error in measuring as small as possible. These measuring cells are conveniently cuvettes The relatively expensive cuvettes are in principle reused. To avoid contaminations and carry-over they must be subjected to complicated cleaning procedures.

However, according to German application DE 195 35 046 C2 the measuring cell can also be a pipette point with two plane-parallel windows which is arranged in the optical path of a photometer integrated into the hand-pipette when affixed thereto. The pipette point can be made from plastic material as an one-time-use article, but this has the disadvantage that it is also relatively complicated in manufacture because of the plane-parallel windows and has a reduced accessability as a special article.

Especially the known optical measuring systems for the measurement of turbidity have the disadvantage to exhibit only a limited measuring range. Extra turbid samples can often be measured only after preceding dilution. However, the dilution of liquid samples is labour intensive and may be problematic because of possible environment-alterations of the cultures. Further, in a relatively large measuring range only a minor differentiation of small concentration differences is recorded. Indeed, this can be remedied to by using special cuvettes with different path-lenghts But this is relatively labour and apparatus expensive.

Departing therefrom the present invention has the objective to provide an optical measuring system for the determination of the concentration, especially of turbid liquid samples, simply to operate and working accurately over a large measuring range and which can be practiced with less expensive measuring cells.

The objective is solved by an optical measuring system with the features of claim 1. Advantageous embodiments of the optical measuring system are indicated in the subclaims.

The optical measuring system for the determination of the concentration especially of turbid liquids comprises:
a measuring volume for taking up the liquid samples to be measured,
a plurality of several photometric channels, each having a light source and a light sensor on different sides of the measuring volume aligned on a common optical axis, and the optical axes therefrom being disposed under different azimutal angles respective to the sample volume, and
an analysing device which evaluates the concentration of the liquid samples to be measured according to the data provided by the light sensors belonging to a plurality of different photometric channels.

Because the measuring data of a plurality of light sensors are drawn on for the determination of the concentration, inaccuratenesses (e.g. optical inhomogeneities, gauge fluctuations etc.) of a measuring cell containing the measuring volume, the walls thereof being irradiated by the photometric channels, which can especially be caused by manufacturing, are less effective in respect to the accurateness of the determined concentration. Consequently measuring cells which are manufactured with relatively little expenditure, and thus may be disposables, can be used Consequently, particularly commercially available vessels (e.g. reaction tanks, pipette points) can be used, which are widely common in laboratory use and the availability thereof is particularly high In principle, measuring cells with different shapes, e g circular or polygonal cross-section, can be used.

Particularly advantageous is the design of the measuring cell as a pipette point made from glass or plastic material. Pipette points are especially wide-spread as one-time-use articles in the plastic material make. They have at one end an aperture for the passage of liquid, and at the other end an aperture for the connection of a pipetting apparatus comprising an expulsion unit. By means of the expulsion unit, an accurately defined liquid volume can be aspirated through the point aperture into the pipette point and subsequently can be ejected again from it. The determination of the concentration in a pipette point has the particular advantage to facilitate the sample handling and to be connectable with an accurate metering of the sample liquid. In this manner one procedure can be saved, because a liquid sample conveniently is pipetted into a cuvette anyway. Also, by simply expulsing the liquid sample from the pipette point, a practically complete and contamination-free recovering of the liquid sample is possible The analysing device can determine the concentration particularly simply based upon an averaging of data of a plurality of light sensors, e.g. based upon an arithmetrical signal averaging.

Preferably, the analysing device can determine, in a first analysing mode, concentrations based upon measuring values provided by the corresponding light sensor of the transmitted light originating from the light source belonging to the same photometric channel as the light sensor. The first analysing mode corresponds to absorption photometry, or turbidimetry respectively, and is preferably selected for an absorption-photometric measurement in the integral measuring range, and for a turbidity measurement in the range of small concentrations.

Furthermore, the analysing device can preferably determine, in a second analysing mode, concentrations based upon data which the corresponding sensor provides of scattered light that originates from at least one light source which is not belonging to the same photometric channel as the light sensor The second analysing mode corresponding to the method of nephelometry can be preferably selected if larger concentrations are to be determined by turbidimetry. In this case the range of larger concentrations can connect immediately to the range of smaller concentrations, respectively the ranges can overlap, so that added together a significantly larger measuring range can be attained by the turbidity measurement. At the same time, a good discernibility of small concentration differences is made possible over the entire measuring range.

In this way the optical measuring system enables the concentration determination of turbid liquid samples to be performed over a wide concentration range Thereby the taking into account of the data of a plurality of photometric channels at the absorption photometric measurement, and at the turbidimetric measurement in the range of smaller concentrations, and the taking into account of a plurality of measuring data of the laterally deflected light of the turbidity measurement in the range of larger concentrations, enables the use of measuring cells with inaccuracies, especially of disposables.

However, the optical measuring system can co-operate with convenient, more accurately produced measuring cells, if the measuring accuracy is to be further improved.

Further, the optical measuring system may comprise a submerged probe, which is submerged into the liquid which is to be measured, so that a liquid sample penetrates into the measuring volume which is situated between the light sources and the light sensors of the submerged probe The submerged probe can especially be tubular. The sample liquid can penetrate through an aperture on the bottom side into the inner space of the submerged probe, where the sample volume is situated. An inner space of the submerged probe comprising the measuring volume can be vented above the photometric channels, so that the sample liquid reaches the measuring volume automatically upon submersion. To protect against contamination, the measuring system of the submerged probe, respectively the photometric channels, can be surrounded by an envelope being transparent in at least the region of the optical measuring. The same can be made interchangeably, especially as a disposable (e.g. of plastic material).

According to another embodiment, in a third analysing mode, the analysing device executes the same determinations as in the first and second analysing mode, and determines the concentrations by combining the results of the two determinations. The third analysing mode is particularly suited for the determination of medium concentrations with turbidity measurements.

Preferably the optical measuring system has a switching device, enabling determination of concentrations according to one of the different analysing modes of the analysing device. This switching device can be manually-operated and adjustable by the user after visual inspection or sample measuring of the liquid sample. But it can be also a switching device which executes a switching between the different ranges automatically, according to whether smaller, larger or medium concentrations are to be determined, respectively For this purpose, in the analysing device e.g. range limits of the concentrations for the use of the different analysing modes can be stored. Then a sample measurement can be performed. If the determined concentration does not fall within the limits of an initially used analysing mode, analysing can automatically be performed with another analysing mode, until a concentration is determined which falls into the limits of the analysing mode used.

According to another embodiment, the optical measuring system can contain a controlling unit which modulates the light sources of the photometric channels, the analysing unit can detect the influence of the ambient light according to the measuring data measured by the light sensors, and eliminate the same upon the determination of the concentrations. The data measured by the light sensors can be evaluated, e.g., using the lock-in principle Another possibility is to make the modulation as large that the light source is temporarily switched out. The signals measured with the light sensors in the dark phases can then be subtracted from those measured in the illuminated phases, thereby eliminating the influence of ambient light.

According to a preferred embodiment, a controlling unit switches on the light sources of the different photometric channels consecutively, in order to avoid cross-over between the different photometric channels. Herewith it is understood with a cross-over that a light sensor of one photometric channel detects a light signal of a light source of another photometric channel, not caused by the scattering of a liquid sample. To avoid cross-over, the light sources of the different photometric channels can be modulated in a phase-shifted manner, so as to switch them on in a temporally interlocked manner. For the same reason, the light sources of the different photometric channels can be modulated with different frequencies, and an unambiguous signal assignment can be performed by frequency analysis. Further, in order to avoid a cross-over the photometric channels can pass through different cross-sectional planes of the measuring volume Photometric channels passing through different cross-sectional planes of the measuring volume can also be present to obtain more data and e g. so further reduce the influence of inaccuracies of a measuring cell upon the measuring result.

Besides, in order to avoid a crossover and for the reduction of ambient light influences, a diaphragm element surrounding the measuring volume or the measuring cell and matching the outer contour thereof can be present, with apertures corresponding to the photometric channels.

The determination of the extinction with absorption photometry, correspondingly of the apparent extinction with turbidimetry, comprises a blank measurement (zero value measurement), that means the determination of the intensity of the transmitted light without the presence of an absorbing or scattering material (blank) in the measuring volume. Further, the determination of the extinction, or the apparent extinction correspondingly, comprises the measurement of the intensity of the emergent (attenuated) light after passing through the absorbing resp. scattering material. Analogous holds for the measurement of the intensity of scattered light with nephelometry. An additional embodiment of the optical measuring device enables to initiate a blank measurement and/or the measurement of an absorbing or scattering liquid sample by actuation of an input unit.

Preferably, the photometric channels are aligned symmetrically towards the measuring volume. Then, the optical axis of neighbouring photometric channels can include identical angles with each other. In this manner the elimination of inaccuracies of the measuring cells is favoured and the evaluation of measuring data is simplified Preferably, an odd number of photometric channels is present, as a result of which it is possible to arrange the light sources and the light sensors consecutively one after the other around the measuring volume. Even in that manner, the elimination of influences of nonuniformity of the measuring cell towards the measurement results is favoured. Preferably, three photometric channels are present which can be arranged starlike around the measuring volume with circular cross-section, to obtain the cited effects with as little expenditure as possible.

As light sources, especially LEDs, and as light sensors, silicon diodes can be used. LEDs are easily modulable.

Silicon diodes can measure even high-frequent signals accurately. Further, these components are inexpensive and space-saving. Preferably the light sources and light sensors can work at 600 nm.

Particularly, the optical measuring system can be a constituent of a pipette, so that a pipette point connected to the pipette is arranged in the optical path of the photometric channels. The optical measuring system also can be, however, an apparatus or part of an apparatus which is not a pipette and exhibits an accommodation means for inserting and removing of a measuring cell. Again, the measuring cell can be a pipette point Preferably, the apparatus, correspondingly its accommodation means, are designed in a manner that a pipette point affixed to a pipette is insertible into the optical path of the photometric channels. The apparatus can comprise means for retaining a pipette with a pipette point. Particularly the apparatus can be a desktop apparatus, into which a pipette is insertible in a similar manner as into a pipette holder. Further, the apparatus can have an input unit, which enables initiation of the measurement procedures by insertion of the measuring cell, e g. with a light barrier or a push-button.

By integration into a pipette, as well as into a separate apparatus, a compact optical measuring installation is realizable which is utilizable directly at the working place. The sample does no more have to be transported to an expensive stationary optical measuring instrument.

The evaluation device and/or the switching device and/or the controlling device(s) are preferably electronic devices.

Figure 2:
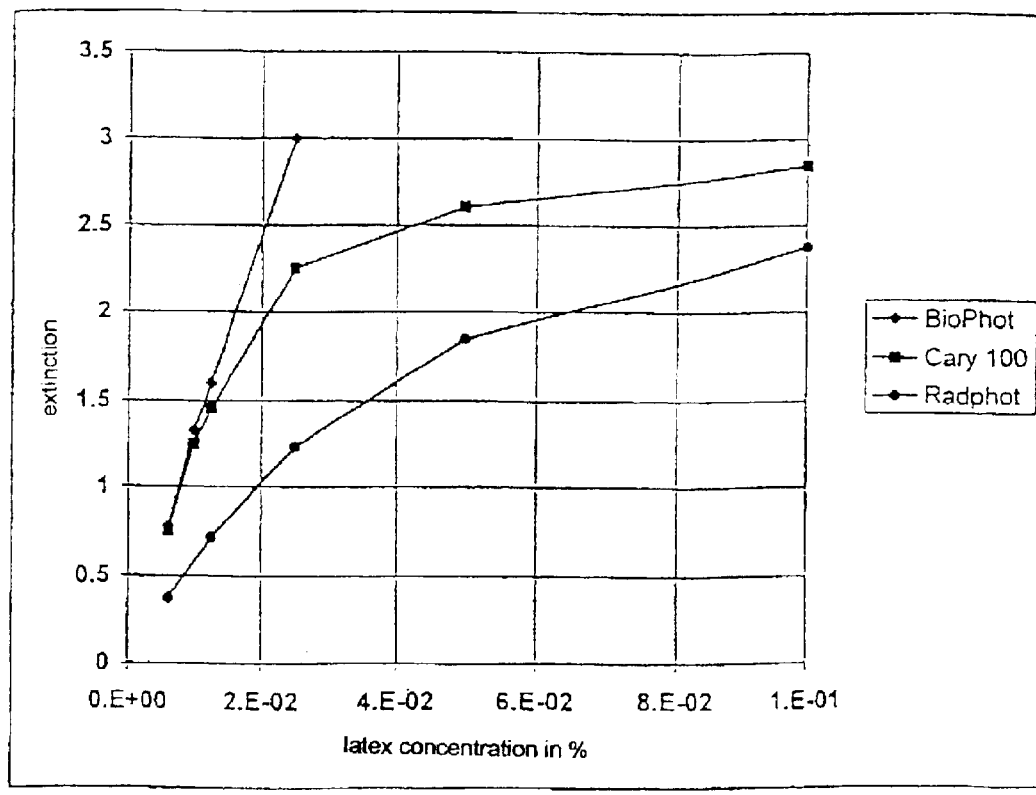
Figure 3:
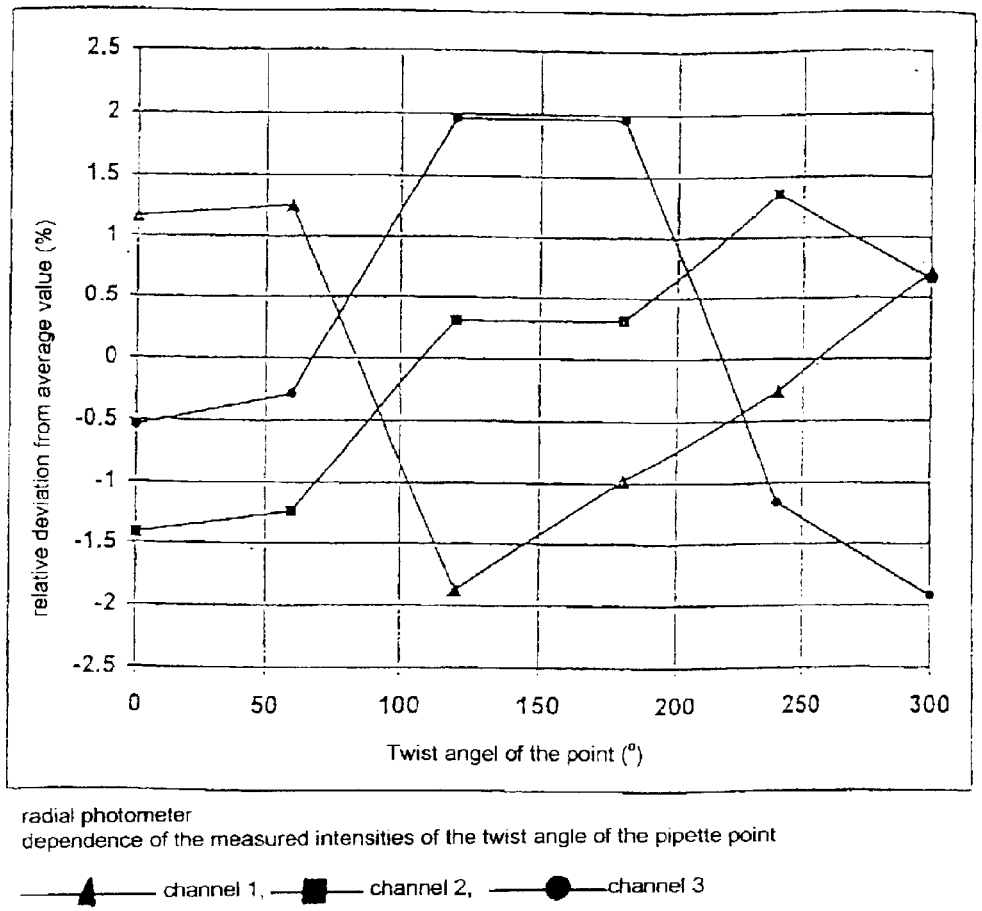
Figure 4:
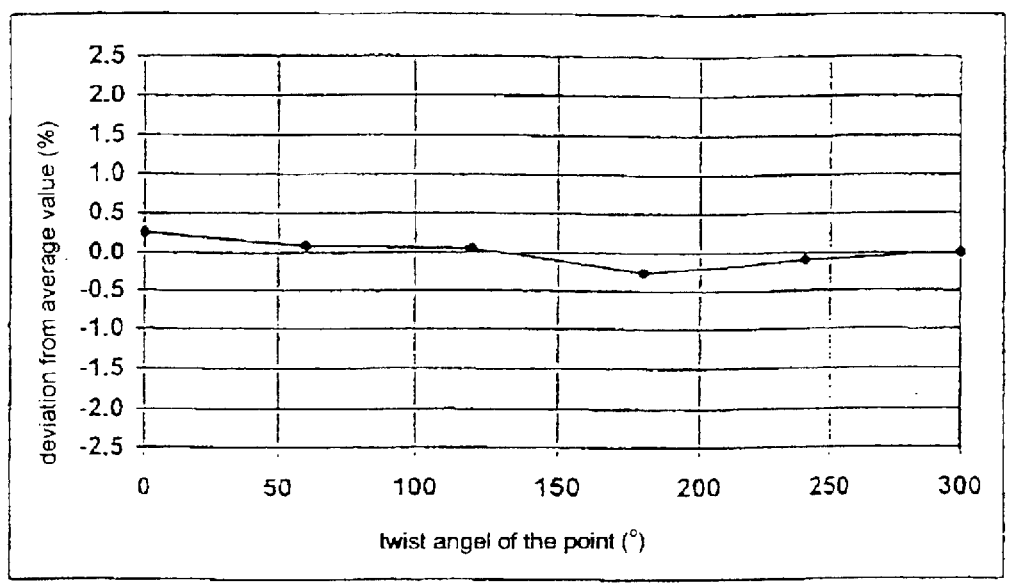

The invention is subsequently explained in more detail with reference to the accompanying drawings of embodiments and measurement results. In the drawings represent:

FIG. 1. Schematic representation of an optical measuring system with a plurality of photometric channels in a cross-section through a measuring cell;

FIG. 2 Dependence of the extinction upon the particle concentration in the sample liquid, when measured using different measuring devices, in a diagram;

FIG. 3 Dependence of the light intensity upon the angle of twist of the pipette point, measured by different photometric channels of the measuring system of FIG. 1, in a diagram;

FIG. 4 Dependence of the average values of measurement signals upon the angle of twist of the pipette point at different particle concentrations, measured by three photometric channels, in a diagram.

Figure 5:
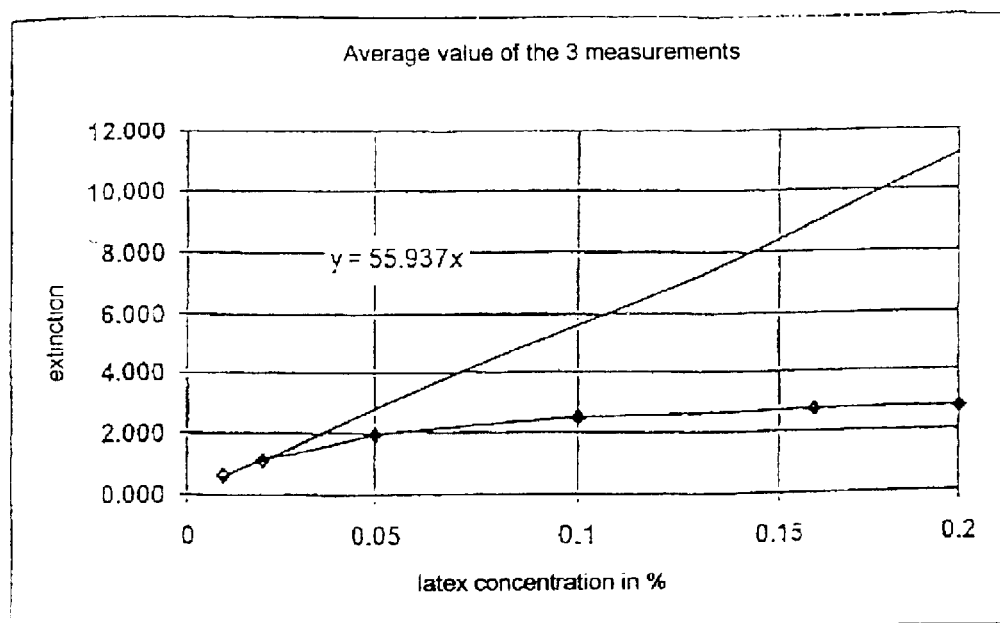
Figure 6:
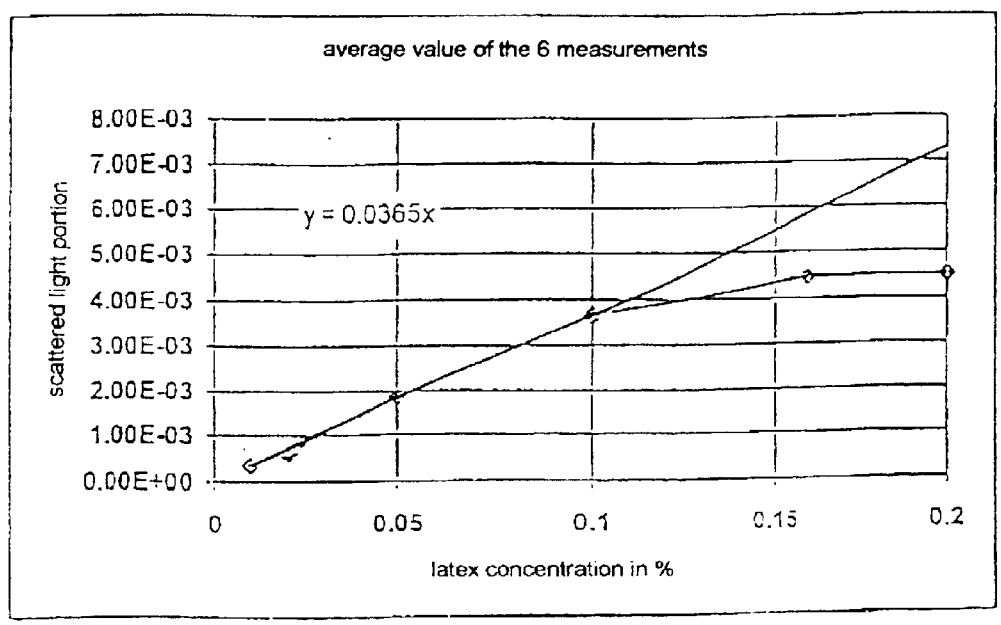
Figure 7:
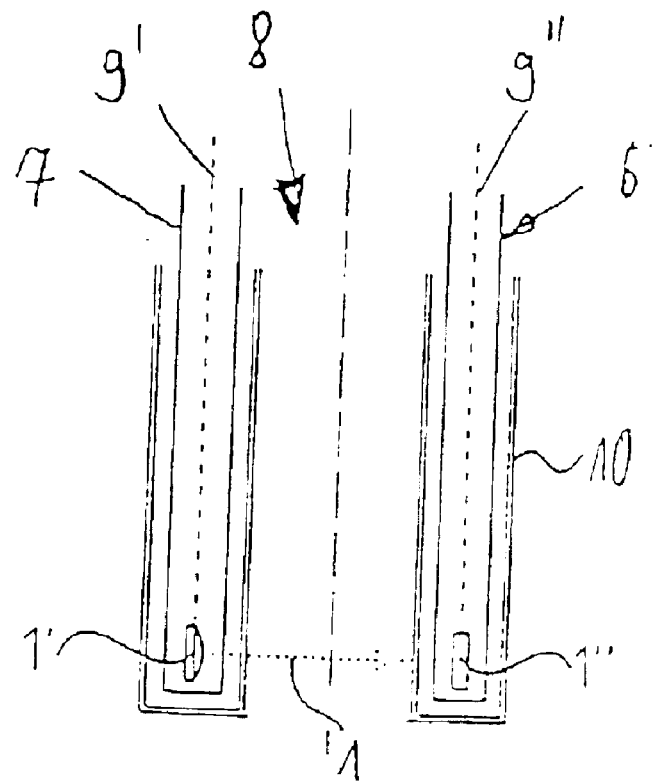
Figure 8:
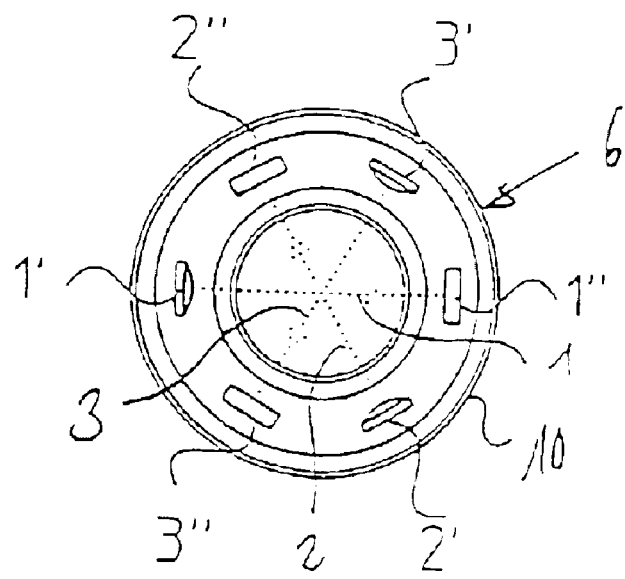

FIG. 5 Dependence of the average value of the extinctions upon the particle concentration, measured by the photometric channels of the optical measuring system according to FIG. 1, in a diagram;

FIG. 6 Dependence of the average value of the scattered light portion upon the particle concentration, measured by different light sensors of the optical measuring system according to FIG. 1, in a diagram;

FIG. 7 Submerged probe of an optical measuring system in a roughly schematic vertical section FIG. 8 The same measuring system in an horizontal section through the plane of the photometric channels.

Figure 9:
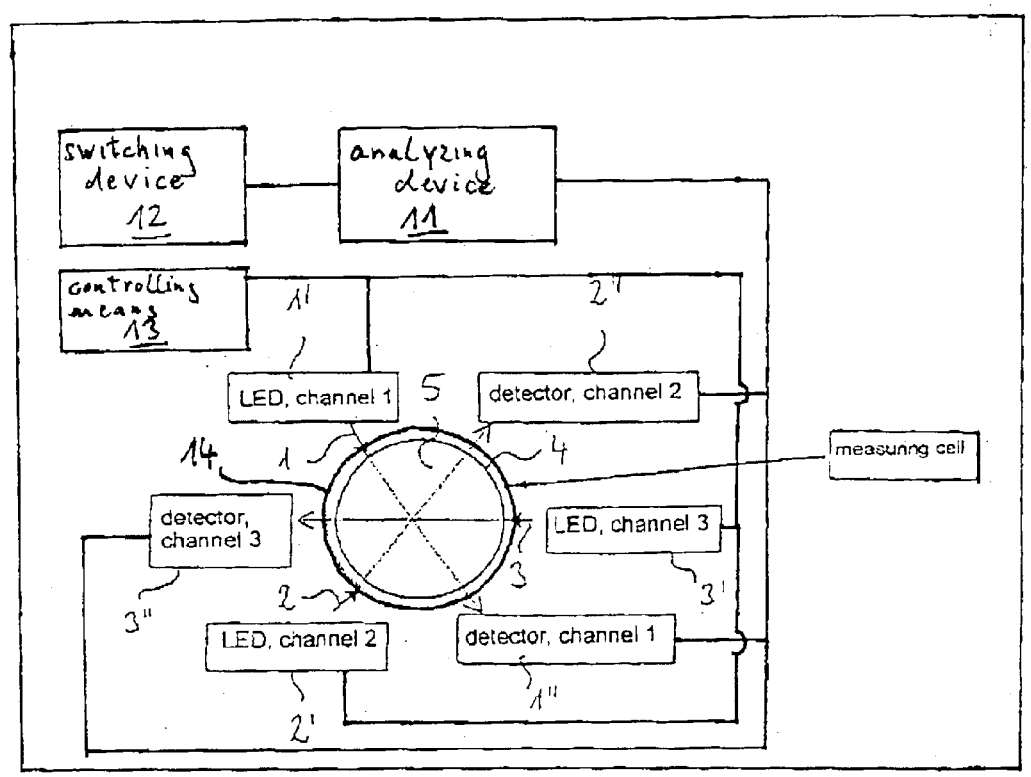

FIG. 9 a schematic representation of a modified embodiment of an optical measuring system according to the present invention.

FIG. 10 Pipette; and

FIG. 11 Pipette Accommodation means.

Upon illumination of a turbid liquid sample, a light scattering is induced by the particles (e.g. cells, bacteria, suspended matter) contained therein. An increase of the concentration of the particles in the solution decreases the intensity of the directionally transmitted light, and increases the intensity of the light scattered into other directions in space.

In biological research, the density of bacteria or cells of a sample is determined in that manner.

Conventionally, the directionally transmitted light is measured as apparent extinction at 600 nm (OD 600). Because the light attenuation determined in this way is caused by scattering, its value strongly depends upon the optical alignment realized in the measuring instrument A comparison of the results of different measuring instruments is therefore only possible via standards.

A relatively wide-band light source, e g. a LED with about 40 nm spectral bandwith, does not significantly influence the measuring results.

The principle of an optical measuring system according to the present invention is explained below, using turbidity measurement as an example. The measuring system is also suited for absorption photometry, however.

According to FIG. 1, N (N>1) photometric channels 1, 2, 3 . . . N are arranged with different azimutal angles (preferably symmetrically) around a measuring cell 4.

Because in FIG. 1 only three photometric channels 1, 2, 3 are represented, only these numbers and the corresponding numbers of the pertinent elements are indicated.

The measuring cell 4 can be circular in cross-section or have N pairs of windows each being parallel to the other (2N-polygon). The light emanating from light-source 1'(e g., a LED) of a photometric channel 1 passes through the transparent wall of the measuring cell 4 to the opposite light sensor (or detector) belonging to that channel.

If the sample contains scattering particles, the light sensor 1 receives attenuated light The apparent extinction determined therefrom is also termed as turbidity. On the other hand, scattered light reaches also the light-sensors 2", 3" of the additional N−1 photometric channels 2, 3. The concentration of particles in the sample determines the turbidity as well as the intensity of the scattered light.

It is also possible to omit in one or several photometric channels 1, 2, 3 light source 1', 2', 3' or light sensor 1", 2", 3" or to replace light source 1', 2', 3' by an additional light sensor 1", 2", 3". Consequently in such a photometric channel 1, 2, 3 turbidity can not be measured. An import compensation function is then inapplicable.

Using the measuring configuration of FIG. 1, concentrations are determined as follows:

The light intensity $I_{11}$ (B) with a blank liquid in the measuring cell and the intensity $I_{11}$ (S) with a sample liquid is measured with the light sensor 1'. From that an apparent extinction (turbidity) $E_1$ of the sample can be determined:

$$E_1 = \log1_{11}(B) - \log1_{11}(P)$$

The same is, provided single scattering (small concentration c of the scattering particles in the liquid), proportional to c:

$$E_1 = k_{10} \cdot c$$

where $k_{10}$ is a proportionality constant.

All the N−1 light sensors 2", 3" not belonging to photometric channel 1, but to photometric channel i (i≠1) measure the intensity $I_{11}(P)$ of light scattered by the scattering particles. The scattered light $I_{11}(B)$ caused by the measuring cell 4 is gathered by the blank measuring and is accounted for. The intensity $I_{11}(B)$ of detector 1 measured with the blank can serve as a reference value for the measured scattered light intensity:

$$S_{li} = \frac{I_{li}(P) - I_{li}(B)}{I_{li}(B)}$$

The measured scattered light intensity depends of the angle included by the optical axis of the photometric channel emitting the light and the optical axis of the photometric channel receiving the light $|\phi|$. The photometric channels 1, 2, 3 can be symmetrically set in the measuring alignment. Thus (N−1)/2 signal pairs are generated having equal $|\phi|$. In order to increase measuring accuracy averaging them is possible:

$$S_{l\phi} = \frac{1}{2}(S_{li(\phi)} + S_{li(-\phi)})$$

At single scattering, this value $S_{1\phi}$ is proportional to the concentration of the scattering particles in a first approximation:

$$S_{1\phi} = k_{1\phi} \cdot c$$

with $k_{1\phi}$ as a proportionality constant.

The correlation between turbidity as well as scattered light intensity and the particle concentration becomes nonlinear with increasing concentration up to reach saturation The utilizable measuring range for certain angles Φ of scattered light measurement is situated at higher particle concentrations, however, than the utilizable measuring range for turbidity measurement, so that both measuring methods supplement A significantly larger measuring range is obtained by this proceeding than in the case that only one method is used The relationships described above for photometric channel 1 are naturally analogously valid for each additional channel of the alignment. In this manner, for turbidity as well as for the scattered light, several data are obtained, which are averaged to compensate for variations of data caused by inhomogeneities of the cross section of measuring cell 4:

$$E = \frac{1}{N}\sum_{i=1}^{N} E_i \quad S_\phi = \frac{1}{N}\sum_{i=1}^{N} S_{i\phi}$$

The averaged proportionality constants $k_o$ and $k_\phi$ are dependent of the shape and diameter of the measuring cell 4 as well as of the specific nature of the scattering sample. They must be determined by calibration. Nonlinearities may be accounted for upon this calibration. The calibration can be performed by, e.g., pouring out a defined amount of sample liquid onto a plane and counting the particles under the microscope, or by other known methods.

To eliminate the influence of ambient light, the intensity of the light sources 1', 2', 3' can be modulated. The light signals registered by the light sensors 1", 2", 3" can then be evaluated by the (specially well known from amplifier art) lock-in principle. Another method consists in making the modulation as large, that the light sources 1', 2', 3' are temporarily switched off. The signals measured in the dark phases with the light sensors 1", 2", 3" are then subtracted from those measured in the illuminated phases. The light sources 1', 2', 3' of the individual photometric channels 1, 2, 3 can be switched on successively. In the second case, the light sources 1', 2', 3' can also be switched on temporarily interlocked.

In the following, the results of turbidity measurements using optical measuring systems with pipette points as measuring cells are represented According to FIG. 1 an alignment is used, where the light emitted from a light transmitter 1', 2', 3' radially hits an opposite detector 1", 2", 3" passing through a pipette point 4. Each alignment comprises three photometric channels 1, 2, 3, which are each constituted of a LED as light transmitter 1', 2', 3' and a silicon detector as light sensor 1", 2", 3".

The light sources 1', 2', 3' are orange-coloured LEDs HLMP-8405 obtainable from Hewlett Packard with a peak wavelength of 600 nm. Si-detectors OSD1-0 of Centronic were used as detectors 1", 2", 3". The LEDs were operated at 1.9 Volts.

The measurement of the detector current was performed with the 350 linear/log optometer of UDT.

The following measurements were performed and results were obtained:

Latex suspensions of different concentrations were used as turbid liquid samples. The diameter of the latex particles was about 0.8 microns. The extinction and transmission values cited refer to water as reference.

For comparison, in FIG. 2 the extinction values of the three photometric channels 1 to 3 of the optical measuring system of FIG. 1, the BioPhotometer® (product of the applicant), and of the Cary 100 (Variant Co.) are represented for various latex concentrations. In both BioPhotometer® and Cary 100 measuring was performed using semimicro plastic cuvettes.

If a plurality of LEDs 1', 2', 3' are operated simultaneously in the optical measuring system of the present invention, light of a light source not related to the corresponding LED 1', 2', 3' may hit a detector 1", 2", 3". This effect can be enhanced by dulled pipette points In table 1 this crossover is demonstrated. Indicated is the ratio of a detector signal to the signal of the detector belonging to the same photometric channel as the luminuferous LED.

It was measured through a water-filled pipette point 4.

TABLE

Crossover on Radial Photometer

| luminuferous LED | dulled pipette point signal ratio | | |
|---|---|---|---|
|  | Det. 1 | Det. 2 | Det. 3 |
| LED 1 | 1 | 1,8E-04 | 1,1E-04 |
| LED 2 | 6,9E-04 | 1 | 7,8E-05 |
| LED 3 | 2,3E-04 | 5,9E-04 | 1 |

Nonuniformities of the pipette point 4 cause the light intensity measured by a photometric channel 1, 2, 3 to be dependent of the irradiation direction through the pipette point 4. In FIG. 3 this dependence is represented for the three photometric channels on a latex suspension.

As well as the three photometric channels, the maxima and minima of the signals are each dislocated to 120° to each other.

By averaging the signals of the three photometric channels in each angle conformation, the direction dependence of the data can be diminished. This is indicated in FIG. 4.

Assuming that a measurement value obtained by averaging in this manner fluctuates with 1% at maximum, the extinction can be obtained with a maximum deviation of ΔE=0.009.

The construction of the optical measuring systems also permits to determine the concentration of the particles via the scattered light For this purpose, simply the signal of the two detectors (e.g. 2", 3") which are not directly hit by the light of the illuminated LED (e.g. 1') has to be evaluated.

The particle concentration is proportional to the portion of the light scattered into the corresponding direction.

As portion of scattered light is denominated here the ratio of the scattered light signal measured by detector (e g. 2", 3") to the signal of the directly illuminated detector (e.g. 1'). The signal of the directly illuminated detector is determined with a water-filled pipette point in this occasion.

It is disadvantageous to dilute densely grown cultures for measuring. To measure even such cultures, the extinction measurement range should be much larger than about E=2. To investigate the measuring limits, supplementaryly latex suspensions with concentrations up to 0.2% were measured.

The results are outlined in FIGS. 5 and 6.

Both diagrams show a significant saturation behaviour whereby the measurable concentration range is limited.

A linear correlation between the extinction, respectively the scattered light, and the particle concentration exists only in a relatively small measurement range. With small latex concentrations, the measuring signal is proportional to the concentration In FIGS. 5 and 6, the measuring values of extinction averaged from the three single signals, and the measuring values of the scattered light portion averaged from the six single signals, and the compensating straight line resulting for small concentrations are represented.

For the extinction, a linearity up to a concentration of about 0.02% can be ascertained. The scattered light portion is linearly proportional to the concentration up to about 0.1%.

If the linear concentration dependence is extrapolated, with a concentration of 0.1% E=5.6 is obtained as extinction. Using the BioPhotometer® an extinction of about 12 would have been measured upon linear extrapolation (cf FIG. 2). Thus, the linear measuring range of the optical measuring system can be significantly enlarged by an additional scattered light measurement, so that even densely grown cultures can be measured.

Comprehensively the following can be stated.

Extinction and scattered light measurings were performed on latex suspensions in pipette points. The measuring apparatus consisted of an arrangement of photometers 1, 2, 3 with LEDs 1', 2', 3' and detectors 1", 2", 3" which were radially aligned around the pipette point 4.

The measured apparent extinctions are in correlation with the results of other photometers The crossover between the measuring channels is negligible The effect of ununiformities of the pipette point could be decreased by averaging of the signals of the three photometers The remaining fluctuation of the extinction is about 0.010.

The radial alignment of the photometers additionally permits the direct measuring of scattered light, the intensity of which is proportional to the concentration of the scattering particles.

According to FIGS. 7 and 8 the optical measuring system exhibits a submerged probe 6 The same has a tubular probe housing 7 with a circular ring-shaped cross section, which can be made essentially hollow in the interior. The photometric channels 1, 2, 3 with light sources 1', 2', 3' and light sensors 1", 2", 3" are aligned on the basis of the probe envelope 7. Thereat, the photometric channels 1, 2, 3 intersect an interior space 8 formed inside the probe housing 7, which contains the measuring volume.

At least in the bottom region of the side directed to the interior space 8 the probe housing 7 is transparent, respectively the light sources 1', 2', 3' and the light sensors 1", 2", 3" are affixed into the walls of the probe housing 7, so as not to obstruct the diffusion of light inside the photometric channels 1, 2, 3.

Electrical cables 9', 9" for the voltage supply, respectively the signal transmission, of the light sources 1', 2', 3' and the light sensors 1", 2", 3" are guided upwards inside the probe housing 7, and can be there connected to an electronic supply- or evaluation device, respectively.

The tubular probe housing 7 can be surrounded, at least in the bottom region, by a complementary-shaped envelope 10, which can be transparent, particularly in the region of the photometric channels 1, 2, 3. The envelope 10 can also be made integrally transparent. Yet it is even possible to make it opaque in the remaining parts, so that it can have the function of a diaphragm at the same time.

The envelope 10 can be made from plastic material. It can further be designed as an interchangeable part. The mounting of the envelope 10 at the probe housing 7 can e.g. occur in a way that it is hold by a slight elastic clamping.

According to FIG. 9, an analyzing device 11 is coupled with detectors 1", 2" and 3" from the optical measuring system of FIG. 1. A switching device 12 enabling switching between the determination of concentrations according to the different modes of the analyzing device 11 is also coupled to the system. Controlling means 13 which modulates the light sources of the photometric channels, 1, 2, 3 is coupled to the light sources 1', 2' 3'. The optical measuring system is provided with accommodation means 14 for inserting and removing the measuring cell 4.

According to FIG. 10, an optical measuring system having photometric channels 1, 2, 3 is constituent of a pipette 15. A pipette tip 4 is connected to pipette 15. Pipette tip 4 is arranged in the optical path of the photometric channels 1, 2, 3.

According to FIG. 11, pipette tip 4', which is connected to pipette 15, inserted into accommodation means 14 of an optical measuring system comprising photometric channels 1, 2, 3. The optical measuring system comprises means (16) for retaining the pipette 15 with pipette tip 4' in the accommodation 14.

What is claimed is:

1. Optical measuring system for determining concentration of turbid liquid samples, comprising:

a measuring volume (5, 8) for taking up the liquid samples to be measured, a plurality of photometric channels (1, 2, 3) each comprising a light source (1', 2', 3') and a light source (1", 2", 3") on opposite sides of the sample volume (5, 8) aligned on a common optical axis, with optical axes (18) thereof being disposed under different azimutal angles relative to the sample volume, and an analyzing device which evaluates the concentration of the liquid samples be measured according to data provided by the light sensors (1", 2", 3"), the analyzing device determining concentrations in a first analyzing mode based upon measuring values provided by a respective light sensor (1", 2"; 3") of scattered light originating from at least one light source not belonging to a same photometric channel (1, 2, 3), the analyzing device determining a concentration based upon an average of the data of a plurality of light sensors (1", 2", 3"), and the analyzing device determining concentrations an a second analyzing mode based upon measuring values provided by a respective light sensor (1", 2", 3") originating from a transmitted light source (1', 2', 3') belonging to a same photometric channel (1, 2, 3), the measuring system further comprising a device for switching between determinations of concentrations according to different modes of the analyzing device.

2. Optical measuring system according to claim 1, wherein the analyzing device performs, in a third analyzing mode, same determinations as in the fist and second modes, determining the concentrations by combination of result, of the first and second modes.

3. Optical measuring system according to claim 1, wherein the switching device automatically executes switching between the different analyzing modes in a manner so that smaller concentrations are determined by the first mode, higher concentrations are determined by the second mode, and medium concentrations are determined by the third mode.

4. Optical measuring system according to claim 1, comprising controlling means which modulates the light sources of the photometric channel (1, 2, 3), the analyzing device detecting influence of an ambient light according to the data measured by light sensors (1", 2", 3") and eliminating same in determination of concentration values.

5. Optical measuring system according to claim 4, wherein the controlling means consecutively switches on the light sources (1', 2', 3') of the plurality of the photometric channels (1, 2, 3).

6. Optical measuring system according to claim 1, wherein at least one of a blank measuring and measuring of the liquid sample can be initiated by activating an input unit.

7. Optical measuring system according to claim 1, wherein the photometric channels (1, 2, 3) are arranged symmetrically relative to the measuring volume (5, 8).

8. Optical measuring system according to claim 1, wherein the plurality of photometric channels (1, 2, 3) comprises three channels.

9. Optical measuring system according to claim 1, wherein the light sources (1', 2', 3') and the light sensors (1", 2", 3") are arranged alternatingly around the measuring volume (5, 8).

10. Optical measuring system according to claim 1, wherein the light source (1', 2', 3') and the light sensors (1", 2", 3") is a silicon diode.

11. Optical measuring system according to claim 10, wherein the light source (1', 2', 3') and light sensor (1", 2", 3") operate at 600 nanometers.

12. Optical measuring system according to claim 1, wherein the measuring volume (5, 8) exhibits a polygonal or round cross-section.

13. Optical measuring system according to claim 1, wherein the measuring volume (5) is arranged in an interchangeable measuring cell (4).

14. Optical measuring system according to claim 13, comprising a diaphragm element surrounding the measuring volume (5, 8) or the measuring cell (4), and matching to an outer contour thereof, with aperture corresponding to the measuring cell (4), and matching to an outer contour thereof, with apertures corresponding to the photometric channel (1, 2, 3).

15. Optical measuring system according to claim 13, wherein the measuring cell (4) is a pipette point.

16. Optical measuring system according to claim 1, which is a constituent of a pipette, with a pipette point being arranged in an optical path of the photometric channels (1, 2, 3).

17. Optical measuring system according to claim 1, which is an instrument with accommodation means for inserting and removing of a measuring cell (4) in an optical path of the photometric channels (1, 2, 3).

18. Optical measuring system according to claim 17, wherein a pipette point (4') affixed to a pipette is insertible into the accommodation means.

19. Optical measuring system according to claim 18, comprising means for retaining the pipette with the pipette point (4').

20. Optical measuring system according to claim 1, comprising a submerged probe (6) submergible into a liquid to be measured, so that a liquid sample penetrates into the measuring volume (8) located between the light sources (1', 2', 3') and the light sensors (1", 2", 3") of the submerged probe.

21. Optical measuring system according to claim 20, wherein the submerged probe (6) is tubular.

22. Optical measuring system according to claim 20, wherein an inner space including the measuring volume (g) of the submerged probe (6) above the photometric channels (1, 2, 3) as vented.

23. Optical measuring system according to claim 20, wherein the submerged probe (6) is at least partially surrounded by an envelope (10) which is transparent at least in a region of the photometric channels (1, 2, 3).

24. Optical measuring system according to claim 23, wherein the envelope (10) is inter changeable.

25. Optical measuring system according to claim 23, wherein the envelope is made of plastic material.

26. Optical measuring system according to claim 23, wherein the envelope (10) forms a diaphragm.

* * * * *